United States Patent [19]

Felcht

[11] 4,348,337
[45] Sep. 7, 1982

[54] PROCESS FOR THE MANUFACTURE OF 1-HALOGEN-1-OXO-$\Delta^3$-PHOSPHOLENES

[75] Inventor: Utz-Hellmuth Felcht, Bruchmühlbach, Fed. Rep. of Germany

[73] Assignee: Hoechst Aktiengesellschaft, Frankfurt am Main, Fed. Rep. of Germany

[21] Appl. No.: 149,741

[22] Filed: May 14, 1980

[30] Foreign Application Priority Data

May 16, 1979 [DE] Fed. Rep. of Germany ....... 2919754

[51] Int. Cl.$^3$ ................................................ C07F 9/34
[52] U.S. Cl. .................................................. 260/543 P
[58] Field of Search ..................................... 260/543 P

[56] References Cited

U.S. PATENT DOCUMENTS

| 3,737,456 | 6/1973 | Smith et al. | 260/543 P |
| 3,751,460 | 8/1973 | Schliebs et al. | 260/543 P |
| 3,803,225 | 4/1974 | Smith et al. | 260/543 P |

FOREIGN PATENT DOCUMENTS

| 631416 | 4/1962 | Belgium . | |
| 1192204 | 1/1966 | Fed. Rep. of Germany . | |
| 1956187 | 5/1971 | Fed. Rep. of Germany . | |
| 1362095 | 4/1963 | France | 260/543 P |

OTHER PUBLICATIONS

Arbuzov et al., "Kinetics of 1-oxo-1-chloro-3-methyl-3-phospholene Isomerization in the Presence of Phosphorus Trichloride" Chemical Abstracts, vol. 79, No. 1, (Jul. 9, 1973), 4726v.
Arbuzov et al., "Isomerization of 1-oxo-1-chlorophospholenes in the Presence of Phosphorus Trichloride" Chemical Abstracts, vol. 77, No. 7, (Aug. 14, 1972), 48580f.
Soviet Reference 173768 to Koliec et al.
K. Hunger, Tetrah. Lett. 47, 5929 (1966).
K. Moedritzer et al., Synth. React. Inorg. Met.-Org. Chem. 5 (1), 45 (1975).
B. A. Arbuzov et al., Izv. Akad. Nauk, SSSR, Ser. Khim., (Engl. Transl.), 1971 (6), 1233.
N. A. Razumova et al., Zh. Obsh. Khim. 33 (3), 783 (1963)=Engl. Transl., p. 771.
K. Dittus in Houben-Weyl, Methoden der organischen Chemie, vol. 6/3, p. 371, ff (1965).
Houben-Weyl, Methoden der organischen Chemie, vol. 14/1 (1963), p. 42/43.
U. Hasserodt et al., Tetrah. 1963 (19), 1563.
B. A. Arbuzov et al., Dokl. Akad. SSSR, (Engl. Transl.) 158 (5), 1047 (1964).
B. A. Arbuzov et al., Izv. Akad. Nauk. SSSR, Ser. Khim. (Engl. Transl.) 1972) (8), 1786.
B. A. Arbuzov et al., Izv. Akad. Nauk. SSSR, Ser. Khim. (Engl. Transl) 1967 (3), 648.
N. A. Razumova et al., Zh. Obsh. Khim., (Engl. Transl.) 40 (12), 2554 (1969).
K. Sasse in Houben-Weyl, Methoden der organischen Chemie, vol. 12/2, p. 13 ff (1963).

*Primary Examiner*—Paul J. Killos
*Attorney, Agent, or Firm*—Curtis, Morris & Safford

[57] ABSTRACT

1-Halogen-1-oxo-$\Delta^3$-phospholenes are produced in isomerically pure form by reacting phosphorus trihalides, 1,2-epoxides and 1,3-dienes in a molar proportion of 1 : greater than 1 : at least 1, without isolation of an intermediate stage and at elevated temperature. The process products are intermediates for the manufacture of fungicides, of additives for mineral oils and polymers and of catalysts for the manufacture of polyurethane foams.

8 Claims, No Drawings

PROCESS FOR THE MANUFACTURE OF 1-HALOGEN-1-OXO-Δ³-PHOSPHOLENES

1-Halogen-1-oxo-Δ³-phospholenes of the formula I

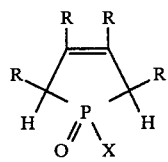

in which the radicals R, which can be identical or different, denote hydrogen, organic radicals and/or halogen and X is halogen are industrially interesting compounds which are important as intermediates for the manufacture of 1-alkoxy(aryloxy)-1-oxo-Δ³-phospholenes. The latter compounds are used as fungicides (cf. DE-OS No. 1,956,187), as additives for mineral oils and polymers (cf. BE-PS No. 631,416) and as catalysts for the manufacture of polyurethane foams (cf. K. Hunger, Tetrahedron Letter 47, 5929 (1966)). Various processes have been described for the manufacture of 1-halogen-1-oxo-Δ³-phospholenes. In principle, they are based on three types of reactions.

$A_I$ In the first type of reaction a phosphorus trihalide II is directly added on a 1,3-diene III and the trihalophosphorane IV is split to the phospholene by means of oxygen-yielding substrates such as water, alcohol or acetone (cf. equations 1a and 1b):

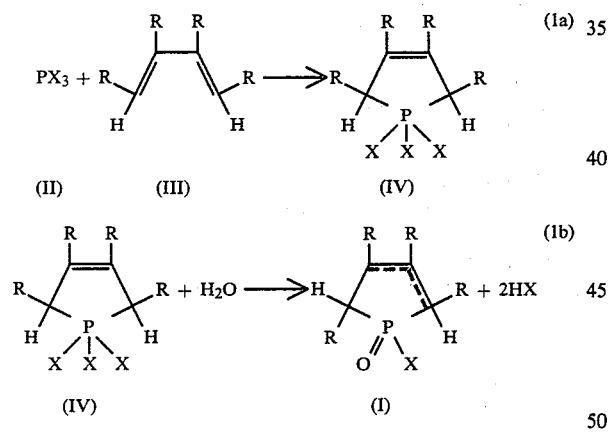

in which R and X are as defined under formula I.

A reaction of this type is described, for example, in DE-PS No. 1,192,204 (for further literature cf. U. Hasserodt, K. Hunger and F. Korte, Tetrahedron 1963(19), 1563; B. A. Arbuzov and A. O. Vizel, Dokl. Akad. SSSR (English translation), 158(5), 1047 (1964) and B. A. Arbuzov, A. O. Vizel, R. S. Giniyatullin and Y. F. Tarenko, Izv. Akad. Nauk. SSSR, Ser. Khim. (English translation) 1972(8), 1786). Because of the long reaction times required of several days to several weeks this process is unsuitable for an industrial manufacture of 1-halogen-1-oxo-Δ³-phospholenes. In addition, the yields are not satisfactory and, therefore, the process is not economic enough. The most serious drawback is the fact that the process furnishes a mixture of the following isomers with respect to the carbon-carbon double bond, indicated in formula I of equation 1b by a dotted line.

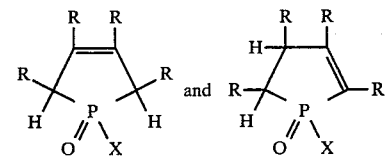

The separation of mixtures of this type of Δ³ and Δ²-isomeric phospholenes, for example by spinning band distillation, requires considerable expenditure of time and material (cf. K. Moedritzer, Syn. React. Inorg. Met.-Org-Chem., 5(1), 45 (1975)).

$B_I$ The second reaction type uses phosphorus acid diester monohalides V which react with dienes, either directly or via intermediate stages, to give 1-halogen-1-oxophospholenes I as shown by the following equations 3, 4a and 4b:

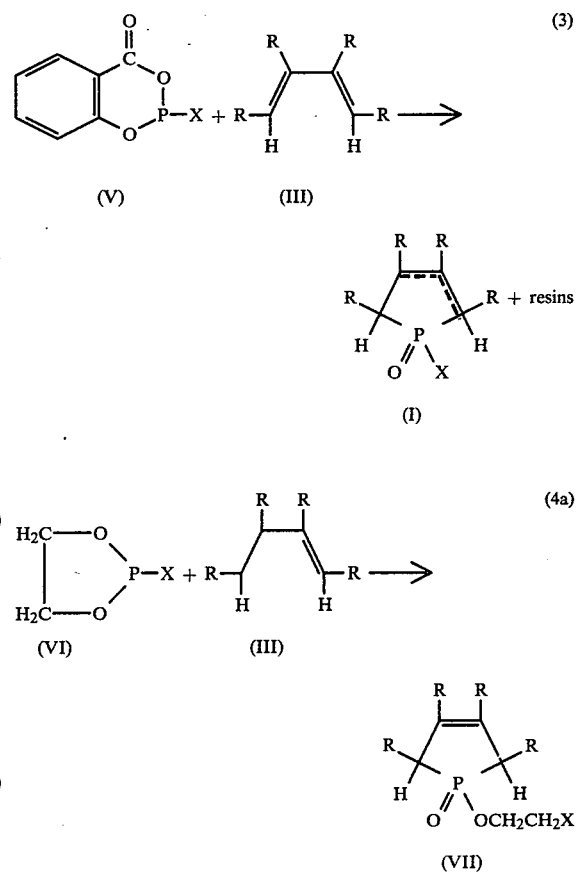

PX₄(OCH₂CH₂X).

In the formulae R and X are as defined under formula I. Both processes are unsuitable for an industrial manufacture of 1-halogen-1-oxo-phospholenes I.

The process according to equation 3 has the disadvantages that large proportions of resinous products are formed and that a mixture of $\Delta^3$ and $\Delta^2$-isomers is obtained. In addition, the starting compound has to be prepared in a preliminary reaction from phosphorus trihalide and salicyclic acid. The multi-stage synthesis requires considerable expenditure of time and material. (cf. B. A. Arbuzov, V. K. Krupnov and A. O. Vizel. Izv. Akad. Nauk. SSSR, Ser. Khim. (English translation) 1971(6), 1233).

The process according to equations 4a and 4b gives moderate yields of 40 to 60% only and requires also a multi-stage synthesis and, therefore, it is not satisfactory either (cf. N. A. Razumova and A. A. Petrov Zh. Obsh. Khim. 33(3), 783 (1963)).

C/ With the third type of reaction some processes start from phosphorous acid monoester dihalides VIII, which are added on 1,3-dienes. The alkyl halide is subsequently split off. The reaction is illustrated by equations 5a and 5b:

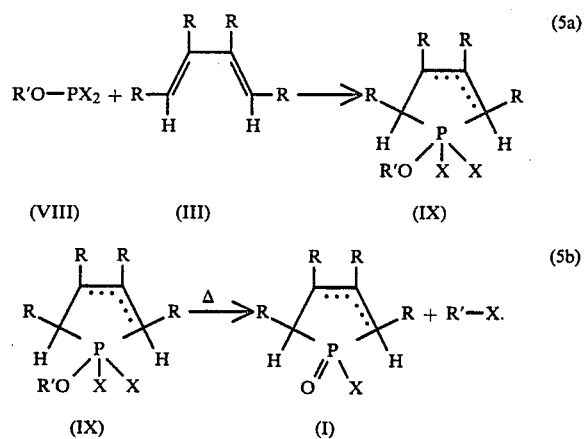

In the formulae R and X are as defined under formula I and R' denotes alkyl or halo-substituted alkyl.

Under definite conditions and if R' is alkyl isomerically pure 1-halogen-1-oxo-$\Delta^3$-phospholenes are obtained (cf. B. A. Arbuzov, A. O. Vizel, Y. Y. Samitov and Y. F. Tarenko, Izv. Akad. Nauk. SSSR, Ser. Khim. (English translation) 1967(3), 658 and N. A. Razumova, L. I. Zubtsova and A. A. Petrov, Zh. Obsh. Khim. (English translation) 40(12), 2554 (1969)), but the yields of about 40% are not satisfactory. A further disadvantage resides in the fact that the phosphorous acid monoester dichlorides must be first synthetized separately by known processes, which requires considerable expenditure of time and material (K. Sasse, Houben-Weyl, Methoden der org. Chemie, edited by G. Thieme, Stuttgart, volume 12/2, pages 13 et seq. (1963)).

In DE-OS No. 1,956,187 a process is described according to which first ethylene oxide and then 1,3-diene are added to an excess amount of phosphorus trichloride (cf. especially Example 8a). In this reaction first a phosphorous acid monoester dichloride is formed which then reacts with the diene (cf. equations 6a to 6c):

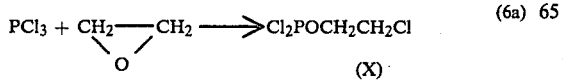

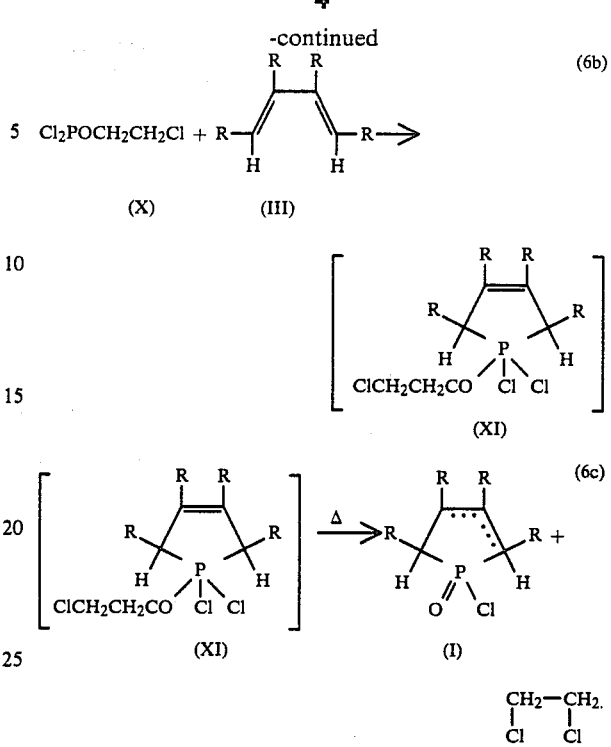

In the formulae R is as defined under formula I.

In this reaction the phosphorous acid β-chloroethyl ester dichloride formed as intermediate need not be isolated and 1-halogen-1-oxophospholenes I are obtained in some sort of "single vessel" process in moderate yields (about 70%). This process has the further drawback, as stated in the above specification and confirmed by experimentation, that mixtures of $\Delta^3$ and $\Delta^2$-halogen-1-oxo-phospholenes are obtained, which involve the separation problems referred to above (cf. equation 2). A mixture of the isomers is also obtained when the phosphorous acid β-chloroethyl ester dichloride is produced by disproportionation of phosphorous acid tris(β-chloroethyl ester) and phosphorus trichloride in the presence of 1,3-diene (cf. Moedritzer, Syn. React. Inorg. Metal-Org. Chem. 5(1), 45(1975) as illustrated by equations 7a and 7b:

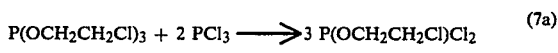

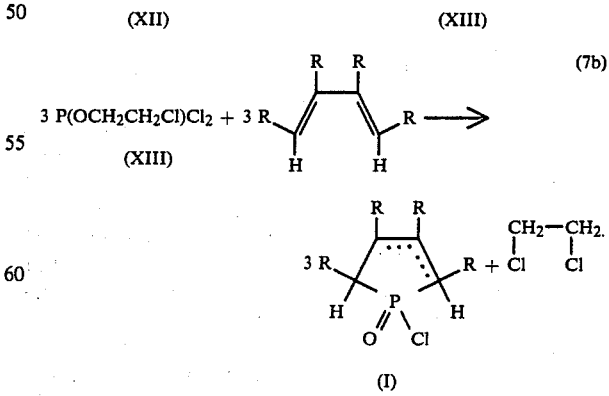

In the endeavour to develop a process producing isomerically pure 1-halogen-1-oxo-$\Delta^3$-phospholenes in very high yield and economic manner is has surprisingly been found that this objective can be achieved in simple and excellent manner by reacting the starting compounds used in DE-OS No. 1,956,187 (cf. equations 6a-6c) in very definite proportions, namely with an excess amount of 1,2-epoxide.

It is an object of the present invention to provide a process for the manufacture of 1-halogen-1-oxo-$\Delta^3$-phospholenes by reacting phosphorus trihalides, 1,2-epoxides and 1,3-dienes, without isolation of an intermediate stage, at elevated temperature, which comprises using the phosphorus trihalide, the 1,2-epoxide and the 1,3-diene in a molar proportion of $1:>1:\geqq 1$. Under these reaction conditions the 1-halogen-1-oxo-$\Delta^3$-phospholenes are obtained in an isomerically pure form.

Suitable phosphorus trihalides in the process of the invention are, in principle, all halides of trivalent phosphorus. It is preferred, however, to use phosphorus trihalides of the formula

 (II)

in which X is fluorine, chlorine, bromine, or iodine, preferably chlorine or bromine.

As 1,2-epoxides all compounds with the oxirane system can be used, preferably compounds of the formula

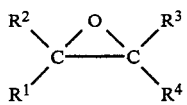 (XIV)

in which $R^1$, $R_2$, $R^3$ and $R^4$, independently of one another, denote hydrogen, $C_1$-$C_{12}$alkyl, preferably $C_1$-$C_4$alkyl, which is optionally substituted by chlorine and/or bromine, $C_5$-$C_7$cycloalkyl or phenyl.

Suitable epoxides are, for example, ethylene oxide, propylene oxide, butylene oxide, 3-chloropropylene oxide, 3-bromopropylene oxide, epoxycyclohexane, epoxycycloheptane, and styrene oxide, which can be prepared by known processes (cf. for example, G. Dittus in Houben-Weyl, Methoden der Org. Chemie, edited by G. Thieme, Stuttgart, volume 6/3, pages 371 et seq. (1965)). Ethylene oxide, propylene oxide and 3-chloropropylene oxide are preferred.

As 1,3-dienes all possible 1,3-dienes can be used, preferably compounds of the formula

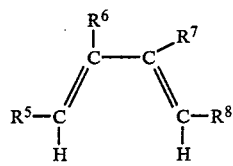 (III)

in which $R^5$ to $R^8$, independently of one another, denote hydrogen, $C_1$-$C_{12}$alkyl, preferably $C_1$-$C_4$alkyl, which is optionally substituted by Cl and/or Br, cyclopentyl, cyclohexyl, phenyl, naphthyl which are optionally substituted by Cl, Br, $C_1$-$C_4$alkyl and/or $C_1$-$C_4$alkoxy, chlorine or bromine.

Suitable dienes are, more particularly, butadiene, isoprene, dimethyl-butadiene, chloroprene, 1-methyl-butadiene, 1-phenyl-butadiene, preferably butadiene, isoprene and 2,3-dimethyl-butadiene.

The process can be carried out in a solvent that is inert to the starting compounds and the reaction products or without such a solvent. Suitable inert solvents are, for example, chlorinated hydrocarbons, especially those having 1 or 2 carbon atoms, such as methylene chloride, chloroform or di- and trichloroethane, aliphatic and aromatic hydrocarbons, especially those having 5 to 8 carbon atoms, for example, heptane, hexane, pentane, or gasoline mixtures with $C_5$-$C_8$aliphatic compounds, benzene, toluene, or xylene.

When in the process of the invention phosphorus trihalides of the formula II, 1,2-epoxides of the formula XIV and dienes of the formula III are used, the reaction proceeds according to the following equation:

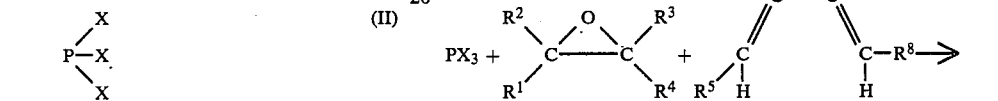

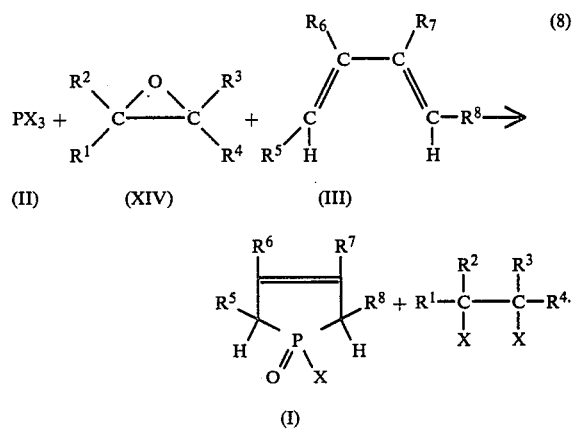

The process of the invention can be carried out in a relatively wide temperature range. In general, temperatures of from about $+50°$ C. to $200°$ C., preferably about $80°$ C. to $140°$ C. are used. The reaction time is generally in the range of from about 3 to 10 hours, preferably about 5 to 8 hours. In general, the process is carried out under an inert gas, mainly nitrogen and argon. In the case of gaseous or readily volatile dienes such as butadiene being used, it is likewise sufficient simply to scavenge the gas space in the reaction vessel by an excess of diene. The proportion of solvent, if any, to the sum of the reactants can be varied within a relatively wide range. In general, a proportion by weight of about 1:1 to 10:1 (solvent: sum of reactants) is used. If liquid reactants are used, it proved advantageous not to use a solvent since in this manner a better utilization of space is ensured.

Usually, the reactants are mixed and the mixture is heated or one of the starting compounds, preferably the 1,3-diene because of its volatility, is introduced into or added dropwise to the mixture of the other reaction components. The sequence of addition of the reactants is, however, not critical.

It proved advantageous to use the phosphorus trihalide and the 1,3-diene in a molar proportion of approximately 1:1, although the diene may also be added in an excess. The molar proportion of phosphorus trihalide to the epoxide used must be 1: more than 1, preferably 1: (1.05 to 1.2), since with too small an amount of 1,2-epoxide a mixture of $\Delta^2$- and $\Delta^3$-isomers is obtained.

If the diene is used in a molar amount less than that of the phosphorus trihalide, which is possible in principle, phosphorous acid $\beta$-haloethyl ester dihalide is additionally isolated from the reaction mixture. In general, the reaction is carried out under pressure, the pressure in the reaction vessel corresponding to the vapor pressure of the volatile constituents at the respective temperature. Usually, polymerization inhibitors are added to the reaction mixture in an amount of from about 0.1 to 1% by weight, calculated on the total weight of the reaction mixture. The suitability of adding such inhibitors, such as, for example, copper stearate, phenothiazine or tert.-butyl-pyrocatechol in the case of reactions of phosphorus chlorides with 1,3-dienes has been reported in the literature (cf. Houben-Weyl, Methoden der org. Chemie, edited by G. Thieme Stuttgart, volume 14/1 (1963)).

When the reaction is terminated the 1-halogen-1-oxo-$\Delta^3$-phospholene is freed by known methods, for example by distillation under reduced pressure, from the solvent, if any, and the 1,2-dihalogenoalkane formed as by-product. In general, the 1-halogen-1-oxo-$\Delta^3$-phospholenes obtained in this manner crystallize in pure form. Normally, a further purification is not necessary; if desired it may be carried out by known methods, for example by distillation under reduced pressure or by sublimation.

The possibility to isolate isomer-free 1-halogen-1-oxo-$\Delta^3$-phospholenes in very good yields by using a slight excess of 1,2-epoxide is extremely surprising since it could not be expected that such a simple measure would give such a result. It is known from processes of the prior art and could be proved by experimentation that the use of the same starting compounds in stoichiometric amounts always yields an isomer mixture of 1-halogen-1-oxo-$\Delta^3$-phospholene and 1-halogen-1-oxo-$\Delta^2$-phospholene which has to be separated with considerable expenditure of time and labor (cf. DE-OS No. 1,956,187 and K. Moedritzer, Syn. React. Inorg. Metal-Org. Chem. 5(1), 45 (1975)). Consequently, the invention represents a considerable progress.

The following examples illustrate the invention.

EXAMPLE 1

A 1 liter glass autoclave with stirrer is charged with 206 g (1.5 mols) of phosphorus trichloride and 0.5 g of copper stearate. 70 g (1.59 mols) of ethylene oxide and thereafter 82 g (1.52 mols) of butadiene are then introduced while stirring. The reaction mixture is heated for 8 hours to 100° C. and for 1 hour to 110° C., cooled and the pressure is released; 1,2-dichloroethane formed is removed at $1.6.10^{-2}$ bar at a bath temperature of up to 80° C. Distillation of the residue furnishes 188 g (91.8% of theoretical) of 1-chloro-1-oxo-$\Delta^3$-phospholene boiling at 82° to 84° C. under $1.0.10^{-3}$ bar, which is free from $\Delta^2$-isomer according to gas chromatographic and $^1$H-NMR spectroscopic analysis.

Comparative Example 1

The reaction of Example 1 is repeated with the exception that 66 g (1.5 mols) only of ethylene oxide are used. Working up and distillation yield 171 g (83.5%) of a mixture of 1-chloro-1-oxo-$\Delta^3$-phospholene and 1-chloro-1-oxo-$\Delta^2$-phospholene which, according to gas chromatographic and $^1$H-NMR-spectroscopic analysis, consists of 73% of $\Delta^3$- and 27% of $\Delta^2$-isomer.

Comparative Example 2

The reaction of Example 1 is repeated with the exception that 60 g (1.36 mols) only of ethylene oxide are used. Working up and distillation yield 166 g (81.0%) of a mixture of 1-chloro-1-oxo-$\Delta^3$-phospholene and 1-chloro-1-oxo-$\Delta^2$-phospholene which, according to gas chromatographic and $^1$H-NMR spectroscopic analysis, consists of 21% of $\Delta^3$- and 79% of $\Delta^2$-isomer.

The results of Example 1 and comparative Examples 1 and 2 teach that with the use of a slight excess of ethylene oxide over the amount of phosphorus trichloride used, the yield of 1-chloro-1-oxo-$\Delta^3$-phospholene is increased while the isomerization to $\Delta^2$-phospholene is fully suppressed.

EXAMPLE 2

The reaction of Example 1 is repeated with the exception that 108 g (2.0 mols) of butadiene are used. Working up and distillation yield 185 g (90.4%) of 1-chloro-1-oxo-$\Delta^3$-phospholene, boiling at 82° C. under $1.0.10^{-3}$ bar, which, according to gas chromatographic and $^1$H-NMR spectroscopic analysis, does not contain any $\Delta^2$-isomer.

A comparison of Examples 1 and 2 teaches that even a larger excess of 1,3-diene is not critical as regards yield and isomer purity of 1-chloro-1-oxo-$\Delta^3$-phospholene.

EXAMPLE 3

An autoclave is charged with 110 g (0.8 mol) of phosphorus trichloride and 0.1 g of copper stearate. 38 g (0.86 mol) of ethylene oxide are introduced and thereafter 61 g (0.9 mol) of isoprene are added dropwise, while stirring. The reaction mixture is heated for 6 hours to 110° C., cooled and 1,2-dichloroethane is removed under $1.6.10^{-2}$ bar up to a bath temperature of 80° C. Distillation of the residue furnishes 103 g (85.5% of theoretical) of 1-chloro-3-methyl-1-oxo-$\Delta^3$-phospholene boiling at 101° to 103° C. under $6.7.10^{-5}$ bar, which, according to $^1$H-NMR spectroscopic analysis is free from $\Delta^2$-isomer.

Comparative Example 3

The reaction of Example 3 is repeated with the exception that 35.2 g (0.80 mol) only of ethylene oxide are used. Working up and distillation furnish 92 g (76.4% of theoretical) of a mixture of 1-chloro-3-methyl-1-oxo-$\Delta^3$-phospholene and 1-chloro-3-methyl-1-oxo $\Delta^2$-phospholene which, according to $^1$H-NMR-spectroscopic analysis, consists of 86% of $\Delta^3$- and 14% of $\Delta^2$-isomer.

Comparative Example 4

The reaction of Example 3 is repeated with the exception that 33 g (0.75 mol) only of ethylene oxide are used. Working up and distillation furnish 88 g (73.1% of theoretical) of 1-chloro-3-methyl-1-oxo-$\Delta^2$-phospholene which, according to $^1$H-NMR-spectroscopis analysis, is free from $\Delta^3$-isomer.

Example 3 and comparative Examples 3 and 4 teach that with the use of isoprene as 1,3-diene a complete isomerization to 1-chloro-3-methyl-1-oxo-$\Delta^2$-phospholene takes place with a small deficiency of ethylene oxide, which fact underlines the importance of the process of the invention for the manufacture of isomerically pure 1-chloro-3-methyl-1-oxo-$\Delta^3$-phospholene.

EXAMPLE 4

460 g (1.5 mols) of phosphorus tribromide and 0.5 g of copper stearate are introduced into a 1 liter glass autoclave provided with stirrer and circulation cooling. While cooling with water and stirring, 70 g (1.59 mols) of ethylene oxide and thereafter 82 g (1.52 mols) of butadiene are introduced. The reaction mixture is heated for 4 hours to 100° C., cooled, the pressure is released and 1,2-dibromoethane is removed under $1.6 \cdot 10^{-2}$ bar up to a bath temperature of 100° C. Distillation of the residue furnishes 186 g (68.5% of theoretical) of 1-bromo-1-oxo-$\Delta^3$-phospholene boiling at 110° to 112° C. under $6.7 \cdot 10^{-5}$ bar, which, according to $^1$H-NMR-spectroscopic analysis, is free from $\Delta^2$-isomer.

EXAMPLE 5

206 g (1.5 mols) of phosphorus trichloride and 0.5 g of copper stearate are introduced into a 1 liter glass autoclave with stirrer. 70 g (1.59 mols) of ethylene oxide are introduced and thereafter 130 g (1.58 mols) of 2,3-dimethylbutadiene are added dropwise while stirring. The reaction mixture is heated for 6 hours to 100° C., cooled, the pressure is released and 1,2-dichloroethane is removed under $1.6 \cdot 10^{-2}$ bar up to a bath temperature of 80° C. Distillation of the residue furnishes 217 g (87.9% of theoretical) of 1-chloro-3,4-dimethyl-1-oxo-$\Delta^3$-phospholene boiling at 102° C. under $6.7 \cdot 10^{-5}$ bar which, according to $^1$H-NMR-spectroscopic analysis, is free from $\Delta^2$-isomer.

EXAMPLE 6

206 g (1.5 mols) of phosphorus trichloride and 0.5 g of copper stearate are introduced into a 1 liter glass autoclave provided with stirrer, an effective condenser and gas inlet. While cooling with water, 70 g (1.59 mols) of ethylene oxide are introduced and thereafter 130 g (1.58 mols) of 2,3-dimethylbutadiene are added dropwise. The reaction mixture is heated to 70° C. while stirring, heated to an internal temperature of 100° C. within 3 hours with decreasing reflux and maintained at that temperature for 2 hours. After cooling 1,2-dichloroethane is removed at $1.6 \cdot 10^{-2}$ bar up to a bath temperature of 80° C. Distillation of the residue furnishes 218 g (88.3% of theoretical) of 1-chloro-3,4-dimethyl-1-oxo-$\Delta^3$-phospholene boiling at 100° to 102° C. under $6.7 \cdot 10^{-5}$ bar which, according to $^1$H-NMR-spectroscopic analysis, is free from $\Delta^2$-isomer.

A comparison of Examples 5 and 6 shows that the process can be carried out at atmospheric pressure without loss in yield if the temperature is slowly increased.

EXAMPLE 7

The reaction of Example 5 is repeated with the exception that 91.6 g (1.58 mols) of propylene oxide are used instead of ethylene oxide. After cooling, 1,2-dichloropropane is removed under $1.6 \cdot 10^{-2}$ bar up to a bath temperature of 100° C. Distillation of the residue furnishes 215 g (87.1% of theoretical) of 1-chloro-3,4-dimethyl-1-oxo-$\Delta^3$-phospholene which, according to $^1$H-NMR-spectroscopic analysis, is free from $\Delta^2$-isomer.

Comparative Example 5

The reaction of Example 7 is repeated with the exception that 84.5 g (1.45 mols) only of propylene oxide are used. Working up and distillation furnish 150 g (60.8% of theoretical) of a mixture of 1-chloro-3,4-dimethyl-1-oxo-$\Delta^3$-phospholene and 1-chloro-3,4-dimethyl-1-oxo-$\Delta^2$-phospholene which, according to $^1$H-NMR-spectroscopic analysis, consists of 78% of $\Delta^3$- and 22% of $\Delta^2$-isomer.

A comparison of Examples 5 and 7 with comparative Example 5 teach that any desired 1,2-epoxide can be used in the process of the invention without the yield being affected and that an isomer-free product can be obtained also with propylene oxide if this compound is used in an excess.

EXAMPLE 8

The reaction of Example 7 is repeated with the exception that the sequence of addition of propylene oxide and 2,3-dimethyl-butadiene is reversed. Working up and distillation furnish 213 g (86.3%) of 1-chloro-3,4-dimethyl-1-oxo-$\Delta^3$-phospholene which, according to $^1$H-NMR-spectroscopic analysis, is free from $\Delta^2$-isomer.

A comparison of Examples 7 and 8 teaches that the sequence of addition of the individual reactants is not critical with respect to yield and isomer purity of the 1-chloro-3,4-dimethyl-1-oxo-$\Delta^3$-phospholene obtained.

EXAMPLE 9

A 5 liter enamelled autoclave is charged with 1,856 g (13.5 mols) of phosphorus trichloride and 3.0 g of copper stearate.

With stirring and circulation cooling 600 g (13.6 mols) of ethylene oxide and then 756 g (14.0 mols) of butadiene are added. The reaction mixture is heated for 5 hours to 90° C., for 5 hours to 100° C. and for 2 hours to 110° C. After cooling, pressure release and withdrawal of the reaction mixture, 1,2-dichloroethane is removed at $1.6 \cdot 10^{-2}$ bar up to a bath temperature of 80° C. Distillation of the residue in a thin layer evaporator furnishes 1,714 g (93% of theoretical) of 1-chloro-1-oxo-$\Delta^3$-phospholene boiling at 82° to 85° C. under $1.0 \cdot 10^{-3}$ bar which, according to $^1$H-NMR-spectroscopic and gaschromatographic analysis, is free from $\Delta^2$-isomer.

What is claimed is:

1. A process for the manufacture of a 1-halogen-1-oxo-$\Delta^3$-phospholene, which comprises reacting a phosphorus trihalide, a 1,2-epoxide and a 1,3-diene, at a temperature of from about 50° to 200° C. and without isolation of an intermediate, the amounts of the phosphorus trihalide, the 1,2-epoxide and the 1,3-diene being in a molar proportion of 1:greater than 1: at least 1, respectively.

2. A process as defined in claim 1, wherein the phosphorus trihalide is a compound of the formula

in which X is fluorine, chlorine, bromine, or iodine.

3. A process as defined in claim 2, wherein X is chlorine or bromine.

4. A process as defined in claim 1 or 2, wherein the 1,2-epoxide is a compound of the formula

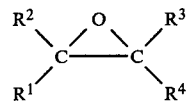

in which $R^1$, $R^2$, $R^3$ and $R^4$, independently of one another, are hydrogen, alkyl of from 1 to 12 carbon atoms, said alkyl substituted by chlorine, bromine or both, cycloalkyl of from 5 to 7 carbon atoms or phenyl.

5. A process as defined in claim 4, wherein the alkyl is of from 1 to 4 carbon atoms.

6. A process as defined in claim 1 or 2, wherein the 1,3-diene is a compound of the formula

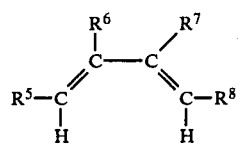

in which $R^5$ to $R^8$, independently of one another, are hydrogen, chlorine, bromine, alkyl of from 1 to 12 carbon atoms, said alkyl substituted by chlorine, bromine or both, cyclopentyl, cyclohexyl, phenyl, naphthyl, or said cyclopentyl, cyclohexyl, phenyl or naphthyl substituted by chlorine, bromine, alkyl of from 1 to 4 carbon atoms, alkoxy of from 1 to 4 carbon atoms, or a combination of said substituents.

7. A process as defined in claim 6, wherein the alkyl is of from 1 to 4 carbon atoms.

8. A process as defined in claim 1 or 2, wherein the reaction is carried out at a temperature of from about 80° to 140° C.

* * * * *